US006905453B2

(12) United States Patent
Grumberg et al.

(10) Patent No.: US 6,905,453 B2
(45) Date of Patent: Jun. 14, 2005

(54) SYSTEM AND METHOD FOR CENTRIFUGAL SEPARATING OF BLOOD COMPONENTS AND FOR SAMPLING THEREFROM

(76) Inventors: Manfred Grumberg, 64 Dania Street, Haifa 34980 (IL); Oren Zinder, 3 Haim Hazzaz Street, Haifa 34996 (IL)

( * ) Notice: Subject to any disclaimer, the term of this patent is extended or adjusted under 35 U.S.C. 154(b) by 49 days.

(21) Appl. No.: 10/352,869

(22) Filed: Jan. 29, 2003

(65) Prior Publication Data

US 2004/0147386 A1 Jul. 29, 2004

(51) Int. Cl.[7] .................................................. B04B 5/02
(52) U.S. Cl. .......................................................... 494/16
(58) Field of Search ............................ 494/10, 16, 20, 494/31, 33, 34, 38, 43, 47–48, 85; 210/781–782; 422/72

(56) References Cited

U.S. PATENT DOCUMENTS

| | | | | |
|---|---|---|---|---|
| 3,096,283 A | * | 7/1963 | Hein | 494/38 |
| 3,190,547 A | * | 6/1965 | Shanley | 422/72 |
| 3,910,547 A | | 10/1975 | Varriano | |
| 5,328,440 A | * | 7/1994 | Chen et al. | 494/10 |
| 6,132,353 A | * | 10/2000 | Winkelman et al. | 494/16 |
| 6,387,277 B1 | * | 5/2002 | North, Jr. | 210/782 |
| 6,398,705 B1 | | 6/2002 | Grumberg et al. | |

FOREIGN PATENT DOCUMENTS

JP 2000-189407 * 7/2000

* cited by examiner

Primary Examiner—Charles E. Cooley
(74) Attorney, Agent, or Firm—Mark M. Friedman

(57) ABSTRACT

A system for separating fluids by centrifuging, the system including: a rotor assembly for rotating in a centrifugation device, the rotor assembly including: (a) a first rotor for housing a plurality of tubes, each of the tubes containing a sample for separation by centrifuging; (b) a second rotor having a plurality of collection compartments, each compartment corresponding to a particular tube, and (c) a plurality of conduits, each corresponding to a particular compartment, each conduit for providing fluid communication, upon demand, between a particular tube and a particular compartment, so as to enable transfer of a fraction of each sample from the tubes to the compartments.

48 Claims, 14 Drawing Sheets

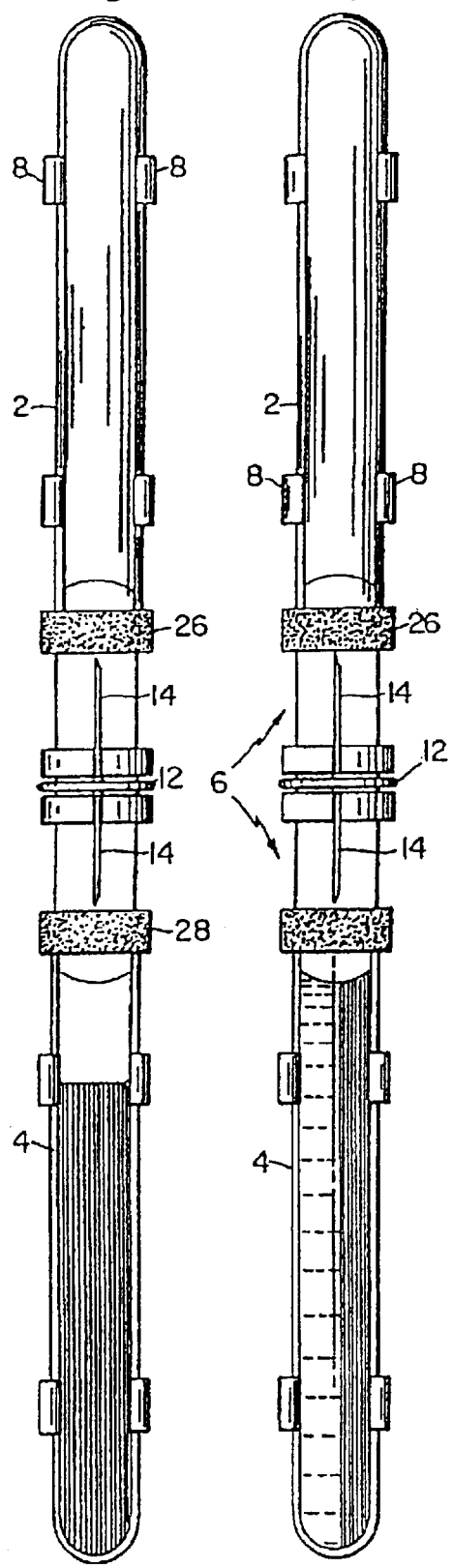
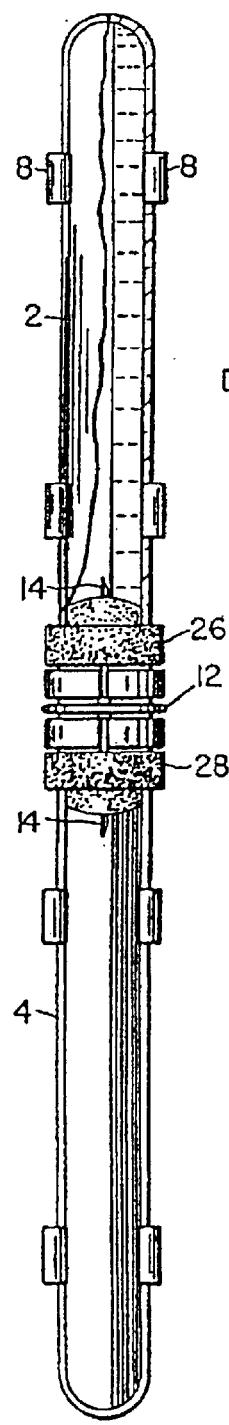
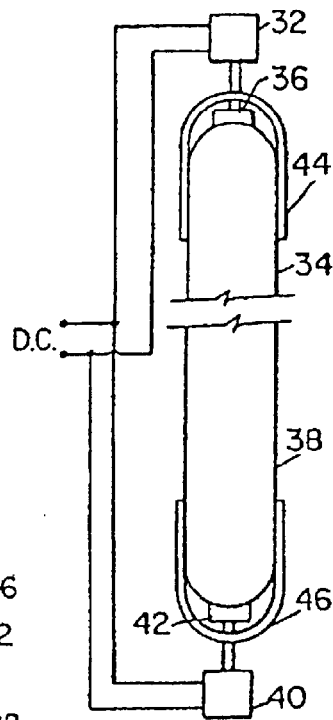
PRIOR ART

SYSTEM AND METHOD FOR CENTRIFUGAL SEPARATING OF BLOOD COMPONENTS AND FOR SAMPLING THEREFROM

FIELD AND BACKGROUND OF THE INVENTION

The present invention relates to the separation of plasma or serum from a blood sample, and more particularly, to a device for achieving such separation in a highly-automated or automation-ready fashion.

In current practice, plasma or serum is typically separated from blood cells of the blood sample by placing whole liquid or clotted blood, respectively, in a tube, and placing the tube in a swinging-bucket type centrifuge. Upon activation, the centrifuge rotates rapidly, causing the tube to acquire a horizontal position. The cells, being heavier than the plasma or serum, migrate to the end of the tube furthest from the center of rotation, thus producing separation of the various components of the sample. In order to form a barrier between the blood constituents after separation, the tube preferably contains a gel that has a specific gravity in between that of the plasma and that of the cells. During the centrifugation, this gel forms a barrier between plasma and cells to prevent remixing when the spin is complete, and the tubes return to their vertical position.

The above procedure is time-consuming, requiring an extended period of centrifugation to achieve the desired results because of the lengthy migration path of the red blood cells along the tube and the need for the gel barrier to form.

U.S. Pat. No. 3,190,547 to J. J. Shanley discloses a centrifuge wherein bottles are located below evacuated plasma receivers. A plurality of such bottle and receiver pairs is rotated about an axis parallel to the axis of each pair, which axis passes through a bottle and receiver. Consequently, upon rotation of the bottles about this axis, red cells migrate toward the outer walls of the sample bottles. Upon completion of the centrifuging, the sample bottle and plasma receivers are connected through hollow needles situated in self-sealing stoppers in each member of the pair, and the plasma is drawn into the plasma receivers. Subsequently, the plasma receivers are spun at a higher rotational velocity (with the specimen bottles being stationary) to produce further separation of the materials drawn therein.

The mechanism is very complex, requiring two separately-driven rotating shafts, two different hollow needles to affect interconnection of the bottle and the receiver, rectangular shaped or other non-cylindrical specimen bottles to ensure that the bottles do not rotate about their own axes. This procedure further requires proper registration of the needle with the sample bottle. To provide proper alignment with the various strata in the specimen bottle, a readily movable self-sealing stopper in the specimen bottle is employed to assist in the search for the strata of the material desired. This procedure may require opening of the specimen bottle to locate the strata interface, thus compromising the sterility of the specimen and possibly endangering the laboratory staff.

U.S. Pat. No. 6,398,705 to Grumberg, et al., teaches a device for rapid separation of plasma or serum from red blood cells. The device includes a rotating drum for spinning a plurality of pairs of head-to-head tubes held in coaxial fashion by a fixture. Each pair of tubes consists of a primary (sample) tube containing a blood sample, and an empty collection tube, under vacuum. The fixture also holds a hollow needle having two sharp ends in between the head-to-head tubes. The tubes must have self-sealing stoppers or caps so that the blood flows only through the needle and does not spin out of the tubes.

When the drum rotates, the red cells migrate to one side of the primary tube. After the separation is completed, and while the centrifuge is still spinning, the two tubes are forced to slide towards each other so that the needle penetrates both stoppers, allowing plasma or serum to flow from the primary tube to the collection tube. The plasma flows into the collection tube due to the partial vacuum in the collection tube and the pressure developed by the centrifuging action in the primary tube.

It must be emphasized that the art disclosed by U.S. Pat. No. 6,398,705 is a significant improvement in relation to the methods and devices previously known in the art, with respect to degree of automation, safety, and separation time. These advances notwithstanding, there remains a great deal of room for improvement. It would be highly desirable to reduce the time required for loading and unloading the plurality of fixtures. It would be highly desirable to reduce the requisite times and labor for assembly and disassembly of each pair of tubes and needle and fixture arrangement.

In common practice, the stopper of the collection tube must be removed to permit sampling of the separated plasma or serum fraction for analysis. In addition to the time and labor expenditures, there is a finite safety risk in removing the stoppers and exposing laboratory personnel to blood samples. Often, this safety risk is compounded by pressure differentials between the collection tube and the environment, resulting in a potentially hazardous aerosol of serum/plasma.

Finally, in transferring the serum/plasma fraction of a blood sample from the sample tube to the corresponding collection tube, care must be taken to preserve the identification of the blood sample on the collection tube (double labeling, etc.). This adds an additional step to the sample preparation process, and perhaps more significantly, introduces an additional possibility for error in a field in which error tolerance is extremely low.

There is thus a widely recognized need for, and it would be highly advantageous to have a device and method for separating blood products that enables a much higher degree of automation and a higher level of safety with respect to the known devices. It would be of particular advantage to have a device that allows for quick and facile sampling by an automatic sample analyzer. It would be of further advantage if such a device would be simple in construction, inexpensive, and easy to manufacture.

SUMMARY OF THE INVENTION

The present invention is a device and method for separating blood products that enables a much higher degree of automation and a higher level of safety with respect to any of the known devices. The separation device is equipped with an analytical extension, disposed within the volume of the collection cell, for in-situ analysis of the separated sample.

According to the teachings of the present invention there is provided a system for separating fluids by centrifuging, the system including: a rotor assembly for rotating in a centrifugation device, the rotor assembly including: (a) a first rotor for housing a plurality of tubes, each containing a sample for separation by centrifuging; (b) a second rotor having a plurality of collection compartments, each corresponding to a particular tube, and (c) a plurality of conduits, each corresponding to a particular compartment, each conduit for providing fluid communication, upon demand, between a particular tube and a particular compartment, so as to enable transfer of a fraction of each sample from the tubes to the compartments.

According to another aspect of the present invention there is provided a system for separating fluids by centrifuging, the system including: a rotor assembly for rotating in a centrifugation device, the rotor assembly including: (a) a rotor having a plurality of collection compartments, integral to the rotor, each compartment for receiving a fraction of a sample separated by the centrifugation device, and (b) a plurality of conduits, each corresponding to a particular compartment, each conduit for transferring the fraction, during a rotation of the centrifugation device, to the compartment.

According to yet another aspect of the present invention there is provided a system for separating fluids by centrifuging, the system including: (a) at least one collection compartment for rotating in a centrifugation device, each compartment for receiving a fraction of a sample separated by the centrifugation device, each compartment including: (i) at least one micro-cell, each micro-cell containing a reagent for effecting an analytical determination on the fraction of the sample, and (b) at least one conduit, each conduit corresponding to a particular compartment, each conduit for transferring the fraction, during a rotation of the centrifugation device, to the compartment.

According to further features in the described preferred embodiments, the compartment is open to an environment, so as to operate at an ambient pressure.

According to still further features in the described preferred embodiments, the compartment has an opening for withdrawing at least a portion of the fraction therefrom.

According to still further features in the described preferred embodiments, the opening is disposed in a top face of the compartment.

According to still further features in the described preferred embodiments, the fraction is a light fraction of the sample.

According to still further features in the described preferred embodiments, each conduit is an integral part of the second rotor.

According to still further features in the described preferred embodiments, the conduit is a hollow needle.

According to still further features in the described preferred embodiments on each tube is disposed a stopper for sealing the tube.

According to still further features in the described preferred embodiments, the compartments are radially spaced around the second rotor.

According to still further features in the described preferred embodiments, the opening is disposed in a radially-inward part of the compartment.

According to still further features in the described preferred embodiments, the conduit has a conduit opening for discharging the fraction to the compartment, and wherein the compartment encloses the conduit opening, so as to prevent any of the fraction from being discharged into an external environment.

According to still further features in the described preferred embodiments, the second rotor further includes a plurality of elements, each element of the elements designed, in a first configuration, to shield a point of the needle.

According to still further features in the described preferred embodiments, the plurality of elements is designed, in a second configuration, to reveal the point of the needle.

According to still further features in the described preferred embodiments, the plurality of elements is spring-loaded.

According to still further features in the described preferred embodiments, the first rotor has a plurality of slots in a side face, to allow reading of an identification label on each of the tubes.

According to still further features in the described preferred embodiments, the second rotor is designed to be reversibly detached from the centrifugation device.

According to still further features in the described preferred embodiments, the first rotor and the second rotor are designed to be reversibly removed from the centrifugation device.

According to still further features in the described preferred embodiments, the first rotor and the second rotor are detachably attached by a connecting mechanism, so as to be removed from the centrifugation device as a single unit.

According to still further features in the described preferred embodiments, the system further includes a mechanism for drawing the first rotor and the second rotor towards one another.

According to still further features in the described preferred embodiments, the system further includes a mechanism for drawing the first rotor and the second rotor towards one another, such that a tip of the needle pierces a stopper sealing the tube.

According to still further features in the described preferred embodiments, each compartment includes at least one micro-cell containing a reagent for effecting an analytical determination on the fraction of the sample.

According to still further features in the described preferred embodiments, at least one of the compartments includes at least one micro-cell containing a reagent for effecting an analytical determination on the fraction of the sample.

According to still further features in the described preferred embodiments, each compartment further includes: (ii) at least one micro-channel, each micro-channel for delivering at least a portion of the fraction to a particular micro-cell.

According to still further features in the described preferred embodiments, each compartment further includes: a rotor assembly for rotating in a centrifugation device, the rotor assembly for housing at least one collection compartment.

According to still further features in the described preferred embodiments, the at least one micro-cell is a plurality of micro-cells.

According to still further features in the described preferred embodiments, the at least one collection compartment has an interface for interfacing with a sample holder assembly.

According to still further features in the described preferred embodiments, the system further includes: (c) a sample holder assembly having a sample holder, the assembly for rotating in the centrifugation device so as to produce the separated fraction of sample, the sample holder fluidly communicating with the conduit, upon demand.

According to still further features in the described preferred embodiments, the micro-channel is designed to receive a second reagent, such that a flow of the sample mixes with the second reagent in the micro-channel prior to reacting with the reagent in the micro-cell.

According to still further features in the described preferred embodiments, the micro-channel has a valve for preventing a return flow from the micro-cell.

According to still further features in the described preferred embodiments, the valve is a flap.

According to still further features in the described preferred embodiments, the valve is responsive to a predetermined pressure differential so as to automatically close the micro-channel.

According to still further features in the described preferred embodiments, the micro-channel has a valve for preventing a return flow of the sample to a central sample volume disposed within the compartment.

According to still further features in the described preferred embodiments, the at least one micro-cell includes a first volume for containing the reagent, and a second volume, fluidly communicating with the first volume, for containing air compressed during the rotation of the centrifugation device.

According to still further features in the described preferred embodiments, the system further includes a valve, associated with the compartment, for preventing a return flow within the compartment.

According to still further features in the described preferred embodiments, the system further includes a valve, disposed within the compartment, for preventing a return flow within the compartment.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

FIG. 1A is a side view of a test tube, fixture and needle arrangement of the prior art, with a partial cross-sectional view showing a whole blood sample within the sample tube;

FIG. 1B shows the arrangement of FIG. 1A, after centrifuging to produce separated blood components;

FIG. 1C shows the positioning of the test tubes in the above-mentioned arrangement, during transfer of a portion of the blood sample to the collection tube;

FIG. 1D is a schematic side view of the above-mentioned arrangement, further including a solenoid mechanism for alternately bringing the tubes together and for separation of the tubes, upon demand;

DESCRIPTION OF THE PREFERRED EMBODIMENTS

Figure 2:
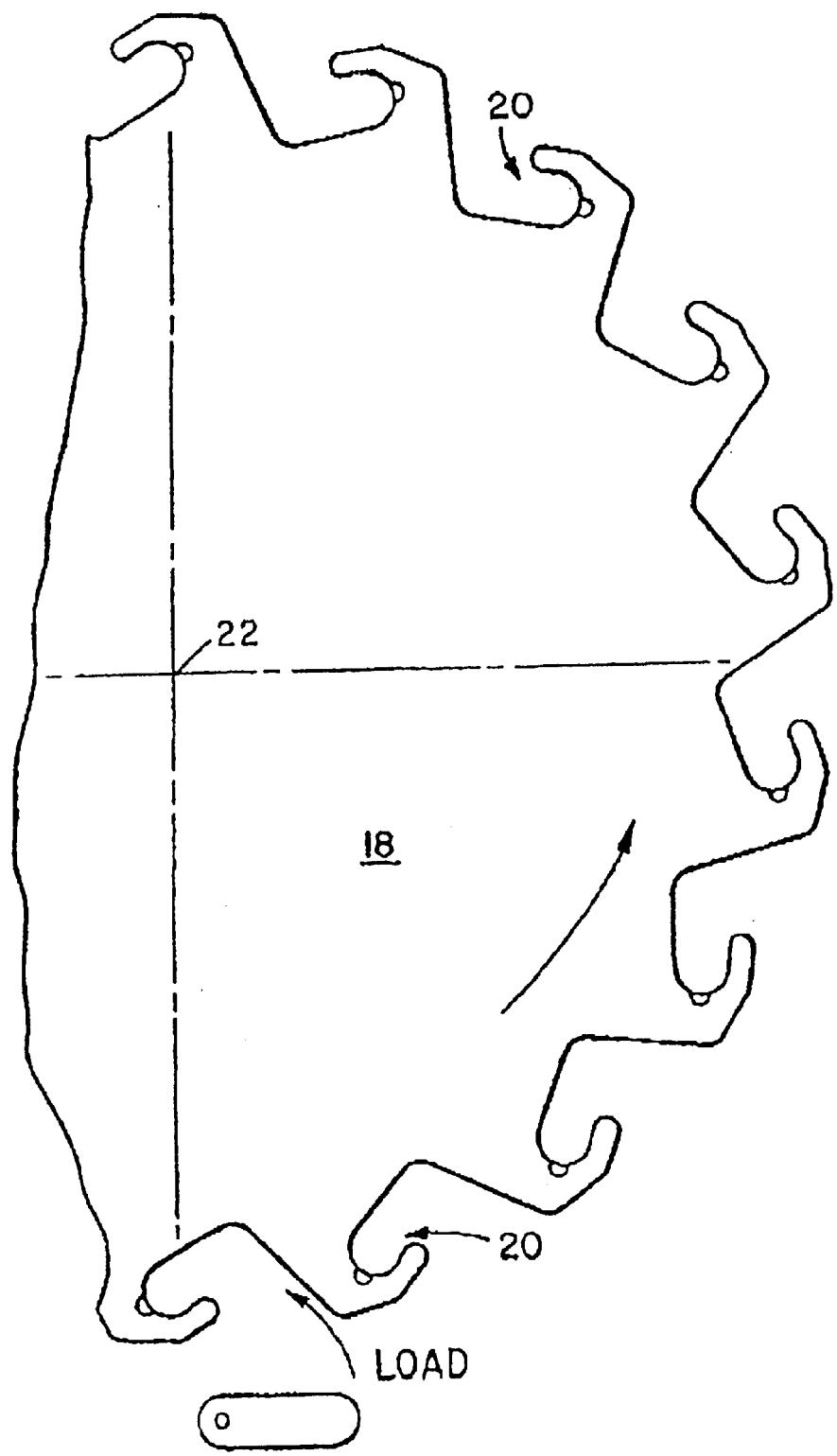
FIG. 2 is a top view of a prior art centrifuge rotor for holding the test tube, fixture and needle arrangement.

The principles and operation of the system in the invention according to the present invention may be better understood with reference to the drawings and the accompanying description.

Before explaining at least one embodiment of the invention in detail, it is to be understood that the invention is not limited in its application to the details of construction and the arrangement of the components set forth in the following description or illustrated in the drawing. The invention is capable of other embodiments or of being practiced or carried out in various ways. Also, it is to be understood that the phraseology and terminology employed herein is for the purpose of description and should not be regarded as limiting.

U.S. Pat. No. 6,398,705 to Grumberg, et al., which is incorporated by reference for all purposes, as if fully set forth herein, teaches a device for rapid separation of plasma or serum from red blood cells. Referring to FIG. 1A of the accompanying drawings, two tubes 2 and 4 are held head-to-head in a fixture 6. The fixture has several sets of opposed spring fingers 8 for grasping the tubes when inserted into fixture 6. Two sets of spring fingers 8 are illustrated for each tube. A needle 14 may be integral with fixture 6. The position of the needle 14 and needle holder 12 is illustrated in FIG. 1A.

The assemblage including tubes 2 and 4, spring fingers 8, needle 14 and needle holder 12 is held together by fixture 6, which is made of a spring-type material. The bevel of the needle is oriented away from the red cells.

FIG. 2 illustrates a portion of a fixture holder 18 of a centrifuge (not shown). Fixture holder 18 has a plurality of receivers 20, each receiver 20 for receiving a fixture (such as fixture 6 shown in FIG. 1A) having the above-described assemblage. The fixtures are situated with the centerline of the tubes and needle parallel to spin center 22 of the centrifuge.

In FIG. 1A, tubes 2 and 4 are fully separated (extended) with liquid or coagulated whole blood in sample tube 4. FIG. 1B illustrates tubes 2 and 4 after centrifuging, with the cells compacted against the region of the tube wall remote from the center of rotation of the centrifuge. The cells constitute only about 37% to a maximum of about 44% in the latter case if the tube is fully filled. Thus, the center of lower tube 4 rarely if ever contains red cells as a result of centrifuging for a time necessary to effect complete separation, one minute or less in a standard size tube.

In FIG. 1C, tubes 2 and 4 have been pushed together, causing needle 14 to penetrate self-sealing stoppers 26 and 28 and establish communication between tubes 2 and 4. The vacuum in tube 2 and the pressure created by centrifuging in the sample tube cause the plasma or serum to be transferred to collection tube 2. Thereafter, the tubes may be separated while the centrifuge is still rotating, the stoppers 26 and 28 sealing their respective tubes. The centrifuge may now be stopped, the fixture(s) with tubes removed, and the tubes processed separately thereafter. If the material remaining in the sample tube is not to be used, the sample tube may also be discarded.

In FIG. 1D, a solenoid 32 is connected to a cap 44 that is disposed about the top of an upper tube 34 of the above-described fixture and tube arrangement. A plate 36 presses on the top of upper tube 34, forcing upper tube 34 towards a lower tube 38. Concurrently, solenoid 40 is energized from a DC current supply 33 to push upper tube 34 and lower tube 38 one against the other, whereby tubes 34 and 38 assume the position illustrated in FIG. 1C.

On the end of each solenoid shaft is an elastic sleeve with plate 36 of solenoid 32 at the upper end of the structure, as illustrated in FIG. 1D. There is a corresponding plate 42 of solenoid 40 disposed inside of sleeve 46. Upon reversal of polarity to the solenoids 32 and 40, the needle (shown in FIGS. 1A–1C) is withdrawn from the tubes.

It must be emphasized that in the art taught by U.S. Pat. No. 6,398,705, each fixture and corresponding assemblage (including sample and collection tubes, stoppers, spring fingers, needle and needle holder) is a separate entity that is individually loaded and unloaded from the centrifuge. Moreover, each fixture and corresponding assemblage must be assembled prior to loading, involving a significant assembly time.

By sharp contrast, the tube assembly of the present invention has a greatly reduced number of components. In addition to the simple and inexpensive construction, the inventive rotor and tube assembly enables a much higher degree of automation and a higher level of safety with respect to the known art. Further advantages will be apparent from the detailed description provided hereinbelow.

Figure 3:
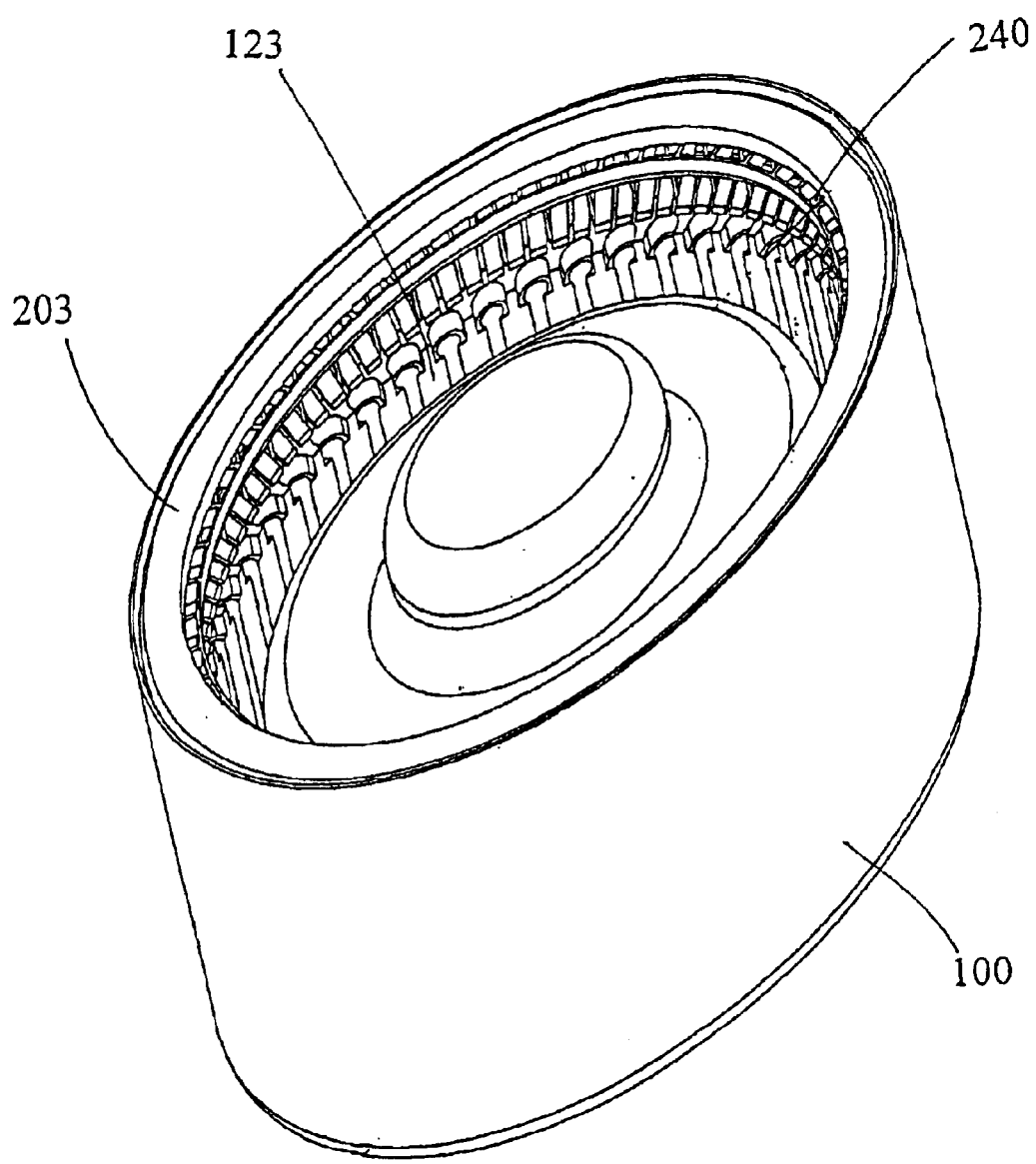
FIG. 3 is a perspective view of the rotor system according to one embodiment of the present invention.

FIG. 3 illustrates the inventive rotor and tube assembly, disposed within a rotating drum 100, according to one embodiment of the present invention. The rotor and tube assembly includes a removable rotor including a bottom ring 123 for holding sample containers, preferably test tubes, with blood samples to be separated, and an upper, collection ring 203 for receiving separated blood products, from the sample containers. Collection ring 203 has a plurality of cells, each having an opening or access port 240 to the environment, preferably covered by a penetrable safety film, through which the separated blood products are sampled/collected by a probe for the purpose of analysis.

Figure 4:
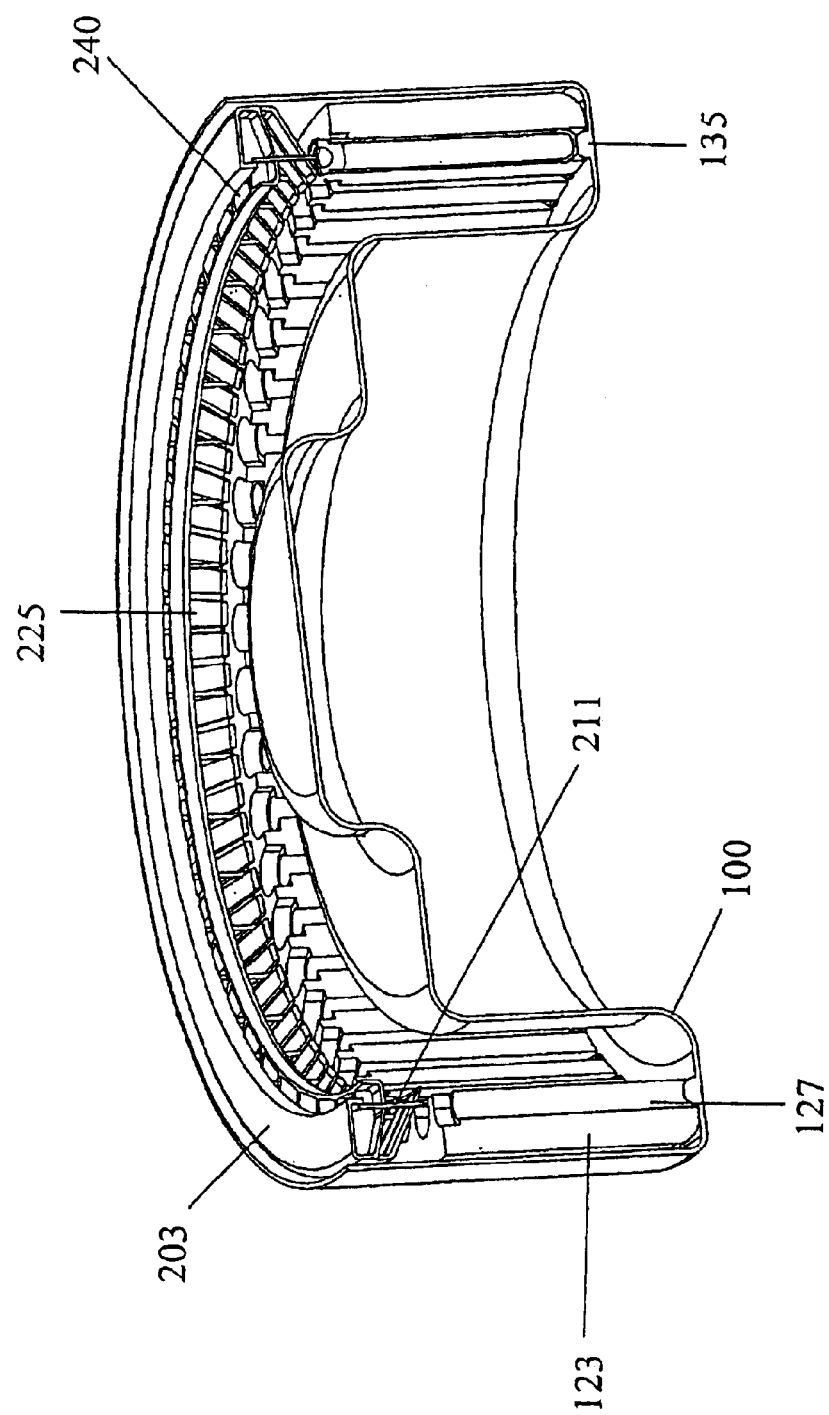
FIG. 4 is a cross-sectional view of the rotor system in FIG. 3, according to one embodiment of the present invention.
Figure 5:
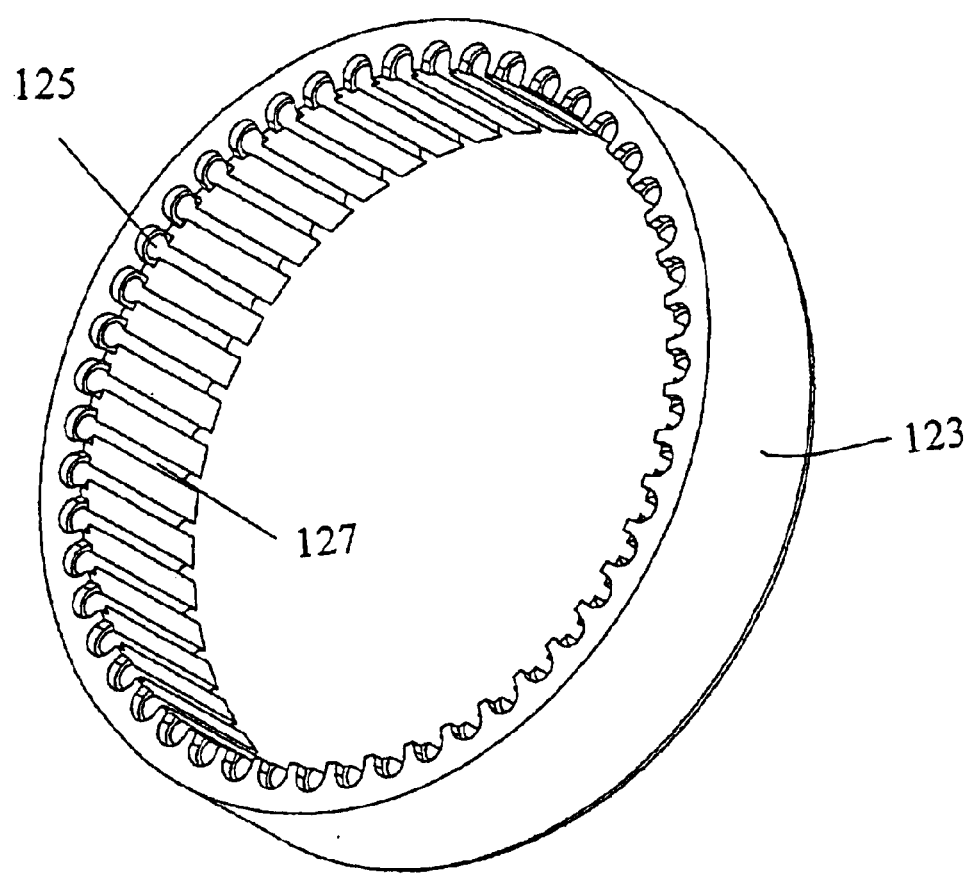
FIG. 5 is a perspective view of the bottom ring of the rotor system according to one embodiment of the present invention.

A schematic perspective view of bottom ring 123 is provided in FIG. 5. Bottom ring 123 contains a plurality of compartments, each compartment 127 configured for receiving a sample container (e.g., a test tube, such as test tube 4 shown in FIG. 1A, and test tube 135 shown in FIG. 4), and flared openings 125 for accommodating test tube stoppers. Bottom ring 123 can be loaded with sample tubes outside of the separation apparatus, or loaded by a manipulator that picks tubes from outside the centrifuge and loads them into bottom ring 123, and discharges the tubes from the centrifuge at the end of the process in a reversed sequence. Sample containers are held in place within each compartment 127 by a snug fit and and/or by centrifugal forces that align the outer surface of each tubes with the outer surface of each compartment 127.

Figure 6:
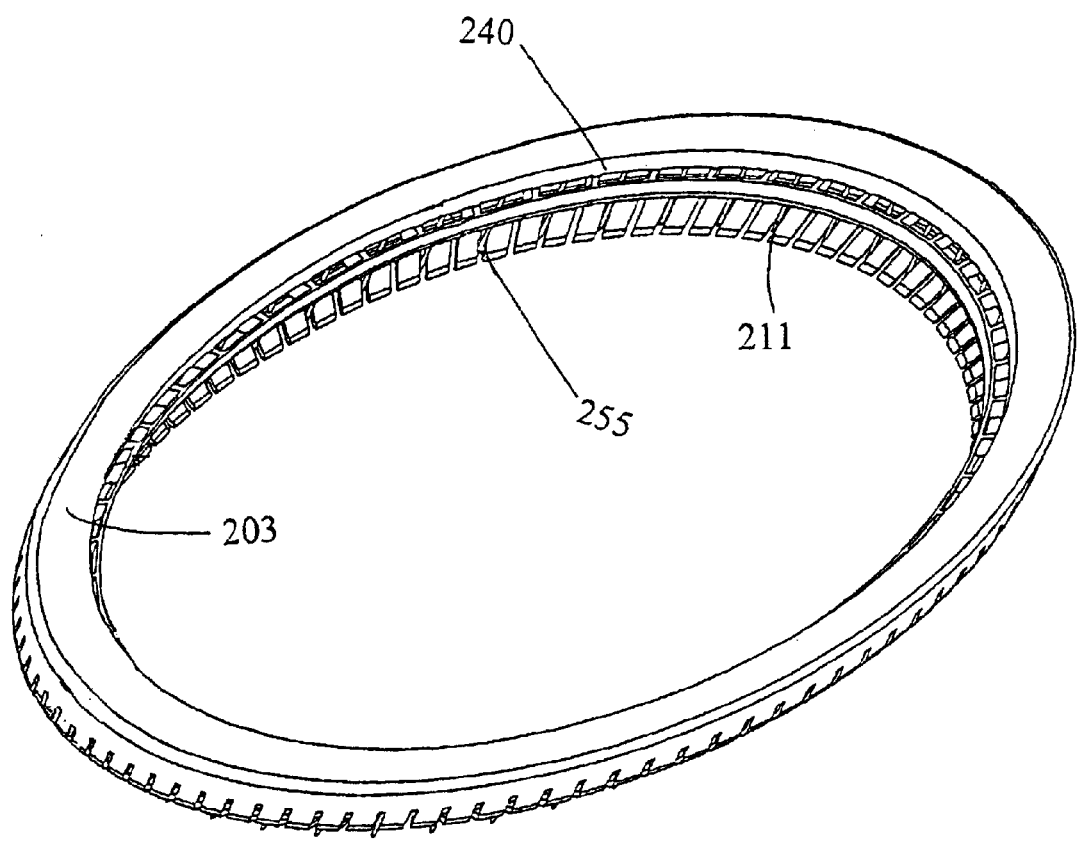
FIG. 6 is a perspective view of the top ring of the rotor system according to one embodiment of the present invention.
Figure 7:
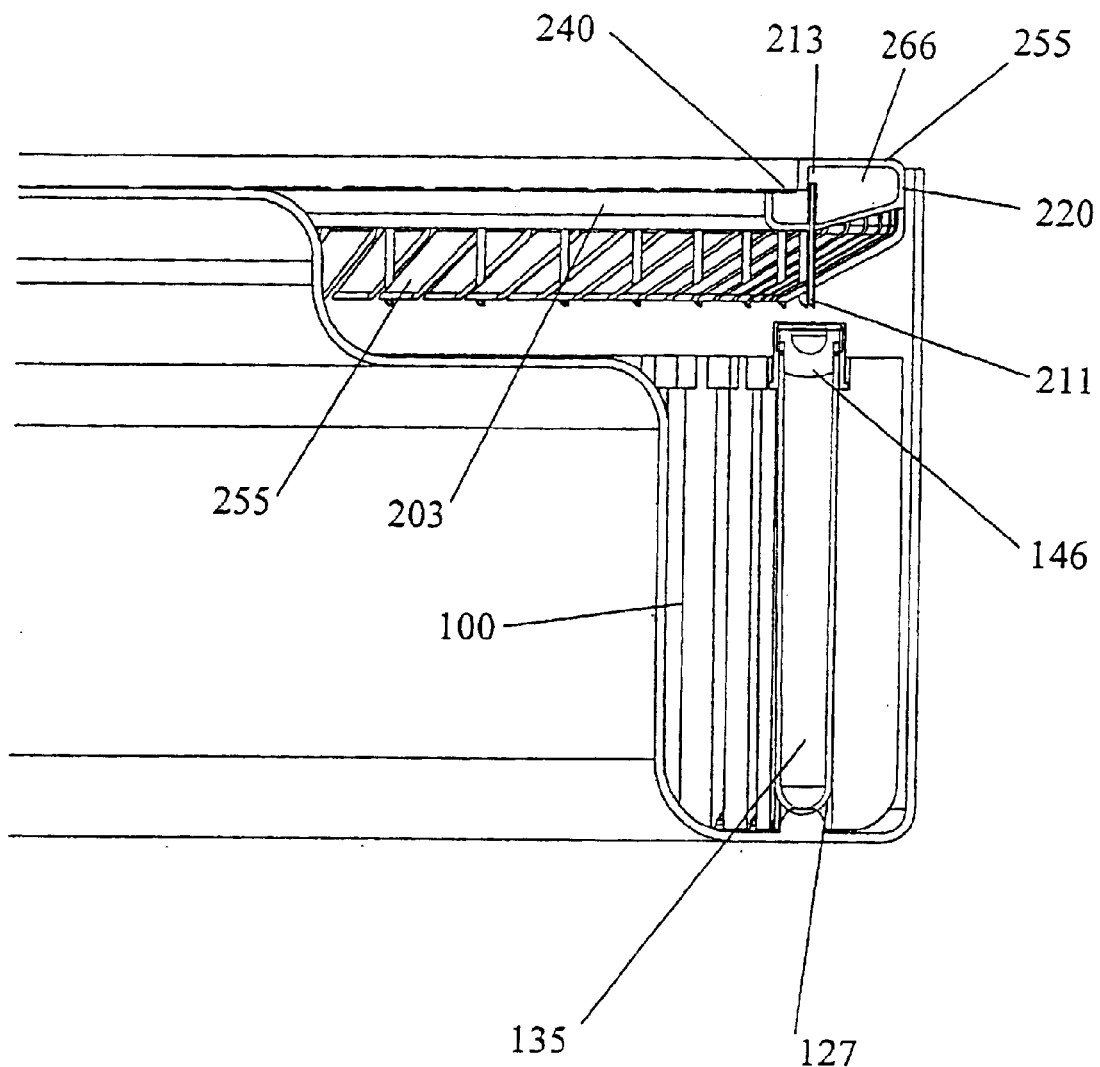
FIG. 7 is a schematic, partially cut-away side view, partially cross-sectional view of the rotor assembly of FIGS. 5 and 6.

A schematic perspective view of top ring 203 is provided in FIG. 6. Collection ring 203 has a plurality of collection chambers (a typical chamber is shown in FIG. 7), each equipped with a hollow needle 211, a spring-loaded needle guard 225 and a chamber sampling opening 240. Each needle 211 is disposed perpendicularly to the face of collection ring 203, with the point facing downwards, towards bottom ring 123. Each sampling opening 240 faces upwards, so as to allow for facile sampling of the material in each collection chamber.

FIG. 7 is a schematic, partially cut-away side view, partially cross-sectional view of the top and bottom rings of FIGS. 5 and 6. Shown in cross-sectional fashion in the foreground are test tube 135 with stopper 146 held within compartment 127. Needle 211, which is integral to collection ring 203, is positioned such that the point of needle 211 is disposed above stopper 146. Alternatively, the point of needle 211 contacts stopper 146, or is partially penetrated so as to be situated within stopper 146 during the centrifugation stage.

At the opposite end of needle 211 is needlehead opening 213, which is disposed within collection chamber 220, such that upon demand, a centrifuged sample can be transferred from test tube 135 to collection chamber 220 via needle 211. Collection chamber or cell 220 has a roof 255, which serves to contain the sample in the event of a forceful discharge of the sample from needlehead opening 213.

Chamber 220 is provided with chamber section 266, disposed outwardly from the center of rotation, for containing separated material, particularly during the centrifugation process, when the material is pushed outwardly by the centrifugal force. Chamber section 266 is completely closed to the environment, thereby preventing the separated material from spraying or leaking out into the room or onto laboratory personnel. To prevent spray during transfer of the specimen to the chamber, opening (access port) 240 can be closed by a thin plastic film or a stopper that can be penetrated by the sampling probe of the analytical instrument. The dimensions of collection chamber 220 are designed such that at rest, the level of the separated material is below chamber sampling opening 240. Preferably, the height of needlehead opening 213 is above the level of the separated material, at rest, to inhibit draining of sample material via needle 211, back into test tube 135.

The centrifugation system of the present invention is operated as follows: a plurality of sample-containing test tubes, such as test tube 135, is loaded into bottom ring 123, which is then inserted into rotating drum 100. Collection ring 203 is then placed on top of/attached to bottom ring 123, such that each test tube 135 aligns with each needle 211 of collection ring 203. Upon joining rings 123 and 203, each spring-loaded needle guard 225 is compressed from a configuration wherein the sharp end of each needle 211 is obscured from an accidental contact by laboratory personnel, into a configuration exposing the needle tip to stopper 145. The exposed tip needle 211 is best viewed in FIG. 7.

Rotating drum 100 is rotated at high speed, so as to separate the blood components in the sample into substantially vertically arranged layers, as shown in FIG. 1B. Subsequently, rings 123 and 203 are pushed towards each other by a mechanism (e.g., the solenoid mechanism provided in FIG. 1D), thereby causing needle to puncture stopper 145 and to penetrate tube 135.

The hydrostatic pressure differential between the pressure (developed during centrifuging) exerted on the sample in tube 135 and the atmospheric pressure of chamber 220 forces sample material disposed below and radially inwards with respect to the tip of needle 211 to enter needle 211 and into collection chamber 220. The heavier component of the sample is disposed radially-outwards with respect to the tip of needle 211, as shown in FIG. 1B, and hence remains in tube 135.

The separated light fraction of the sample is introduced into collection chamber 220 via needlehead opening 213. As rotating drum 100 continues to spin, the separated light fraction is pushed outwardly by the centrifugal force into chamber section 266. As rotating drum 100 comes to rest, the separated fraction comes to rest at the bottom of collection chamber 220, with the level of the separated fraction just below chamber sampling opening 240.

After rotating drum 100 is completely at rest, lab personnel or an automated assay machine can access the sample material through chamber sampling opening 240. The sampling may be performed with collection ring 203 situated within rotating drum 100, or alternatively, collection ring 203 may be removed for sampling, e.g., to a laboratory bench, to a sampling carousel (rotating tray), etc.

According to one embodiment of the present invention, the rotor assembly is designed such that the entire process of loading bottom ring 123 with sample-containing test tubes, and the adjoining of collection ring 203 to bottom ring 123, can be performed outside of rotating drum 100. This is more convenient and efficient in many cases. Perhaps more importantly, each rotating drum 100 can be equipped with two or more rotor assemblies, allowing laboratories having a backlog of samples queued up for centrifuging to prepare and load samples into the second rotor assembly while rotating drum 100 is in use with the first rotor assembly containing a previous batch of samples.

Preferably, bottom ring 123 has an opening or slot associated with each compartment 127 for holding each test tube 135. These slots allow for facile use of bar codes, or other labeling systems, for identification of test tube 135 and association with pertinent patient information. The slots are disposed so as to allow for easy manual reading of the labels by personnel, or for automatic reading by a machine. In the event that the rotor assembly is removed as a unit for analysis, a second, identical label for placing on the corresponding collection chamber is superfluous, as a single label on each test tube 135 is sufficient. Although the slots in FIG. 5 are disposed on the interior face of bottom ring 123, it may be advantageous to provide slots on the exterior face of bottom ring 123, particularly if collection ring 203 and bottom ring 123 are removed from as a unit for sampling and analysis outside of rotating drum 100. The design of the slots may be such that test tube 135 can be pushed into or removed from the slot in a radial or vertical manner.

Rings 123 and 203 may be manufactured by injection molding, stamping, or other manufacturing methods known in the art. Needles 211 may be manufactured as part of the collection ring. Alternatively, each needle 211 is manufactured separately (e.g., metal needles) and molded into a respective collection chamber 220.

Spring-loaded guard 225 is designed to shield the sharp end of needle 211 while collection ring 203 is separated from ring 123, e.g., prior to assembly with ring 123. Similarly, after disassembly (e.g., prior to sampling outside of rotating drum 100, during washing and sterilization, etc.), the sharp end of needle 211 is inherently shielded from accidental contact with laboratory personnel (or surfaces within the laboratory) by the decompressing action of spring-loaded guard 225.

Figure 8A:
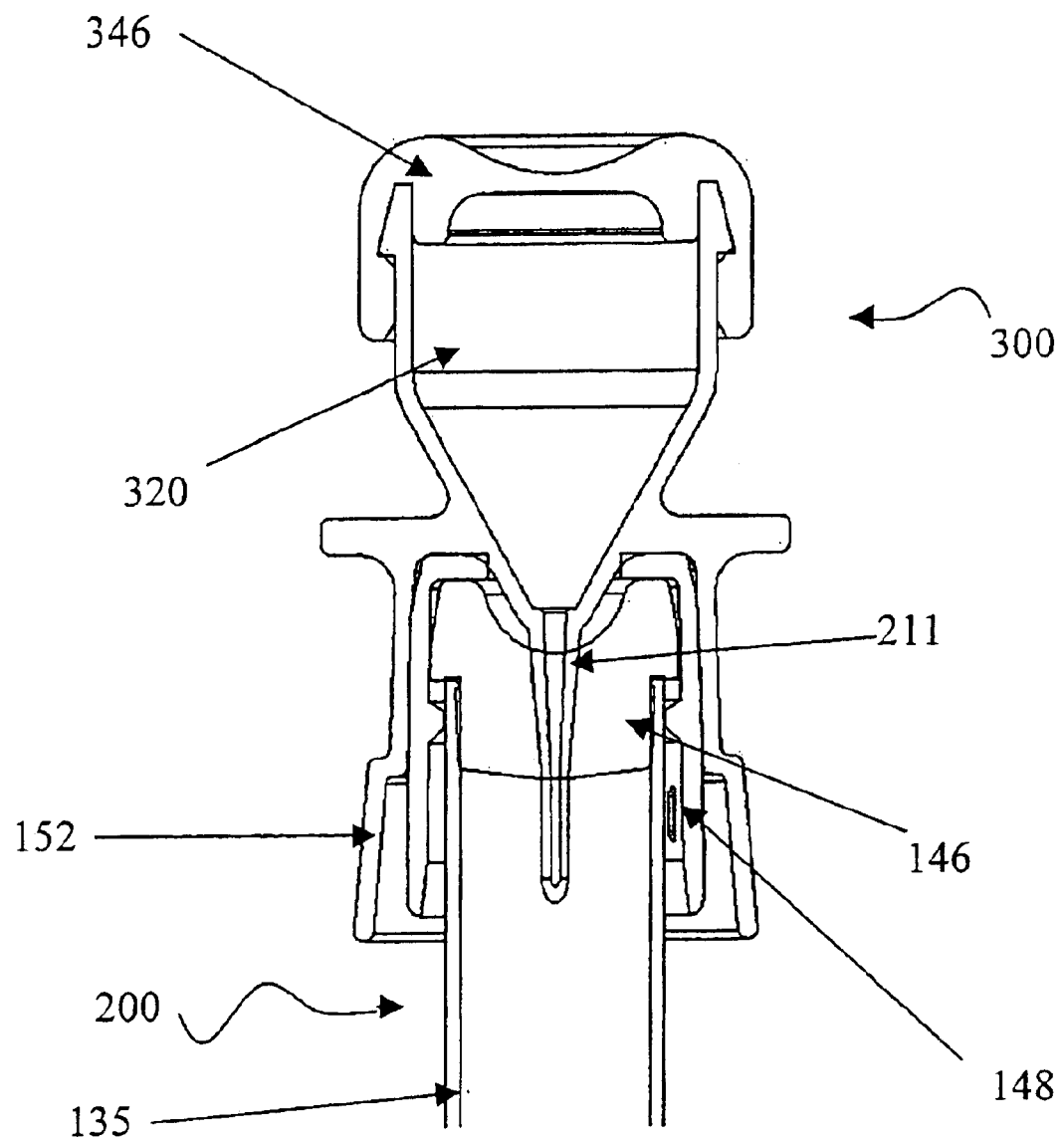
FIG. 8A is a schematic, cross-sectional view of a collection cell interfacing with a test tube assembly, according to one embodiment of the present invention.

FIG. 8A is a schematic, cross-sectional view of a collection cell assembly 320 interfacing with a test tube assembly 200, according to another embodiment of the present invention. Primary tube 135 is sealed by rubber stopper 146. A flexible plastic lock 148 is preferably used to fix stopper 146 with respect to primary tube 135.

Collection cell assembly 300 includes collection cell 320, which has a top opening sealed by upper stopper 346. A hollow needle 211 is fixed at the bottom of collection cell 320, such that the sharp end of needle 211 protrudes below collection cell 320, in the direction of rubber stopper 146. A protective skirt 152 envelops collection cell 320, with the bottom of skirt 152 extending below the sharp end of needle 211 to protect from accidental contact with the sharp end as well as from any blood sample disposed on needle 211.

In FIG. 8A, collection cell assembly 300 is disposed in a depressed position (i.e., after separation of the blood components has been effected), wherein needle 211 has penetrated rubber stopper 146 so as to fluidly communicate between primary tube 135 and collection cell 320. Preferably, at least a portion of the inner surface of protective skirt 152 conforms to the outer surface of flexible plastic lock 148, so as to achieve a snug fit therebetween.

After the separated light fraction of the sample is transferred into collection cell 320 via hollow needle 211, sampling of the separated fraction in collection cell 320 is preferably performed by penetration of upper stopper 346 (e.g., directly by a test probe).

Figure 8B:
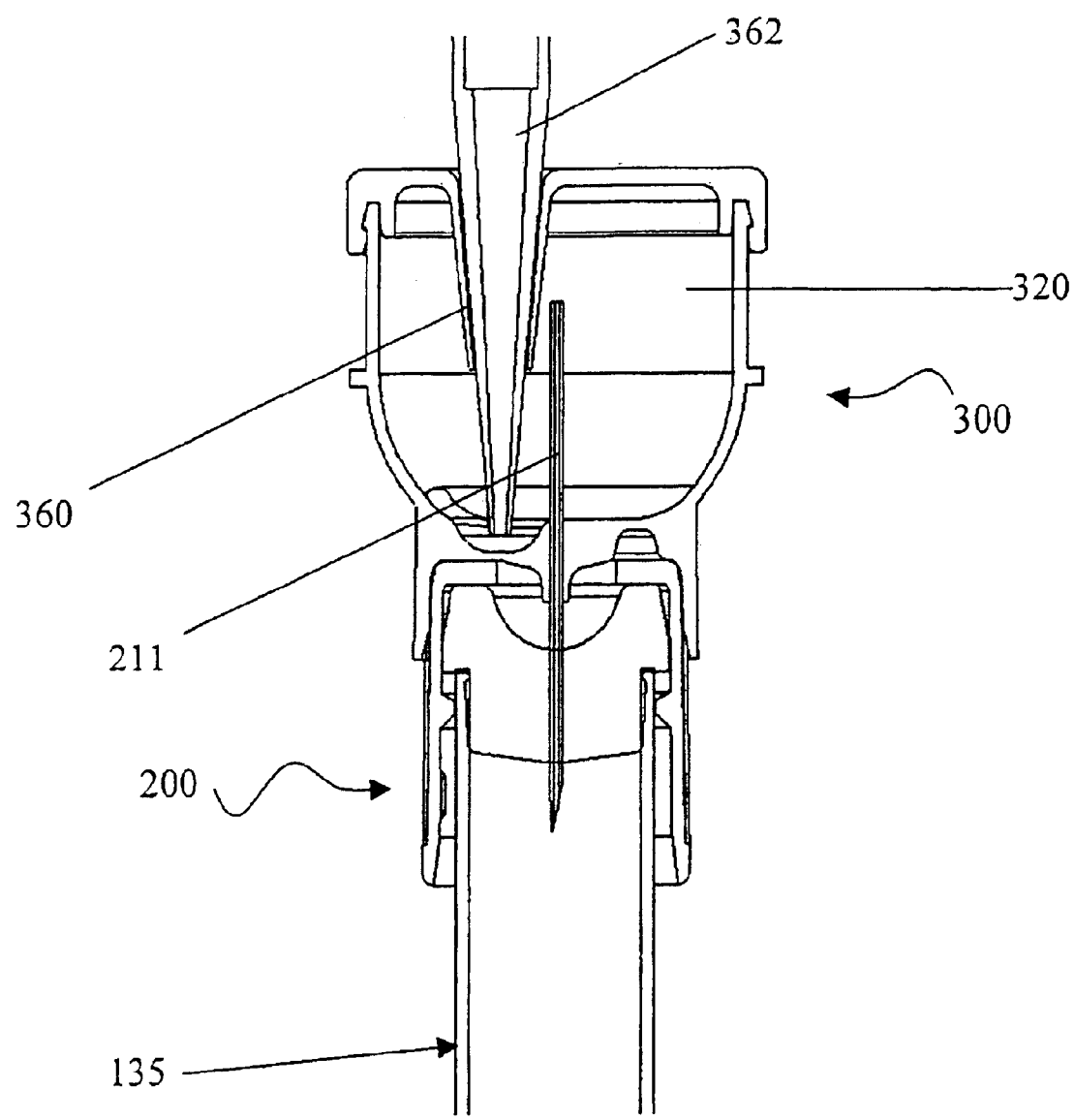
FIG. 8B is a schematic, cross-sectional view of another inventive embodiment of a collection cell interfacing with a test tube assembly, in which the collection cell has a recessed opening for receiving a probe.

A cross-sectional view of another inventive embodiment of a collection cell 300 interfacing with a test tube assembly 200, in which the collection cell has a recessed opening 360 for receiving a probe 362, is provided in FIG. 8B. Probe 362 is inserted into collection cell 320 for sampling and/or analyzing the cell contents. Preferably, the inside geometry of collection cell 320 is designed such that the level of fluid within is always below the level of recessed opening 360, irrespective of cell orientation. This substantially prevents the contents of collection cell 320 from spilling out, in the event that collection cell 320 is tipped over on a side, or even completely turned over.

Figure 8C:
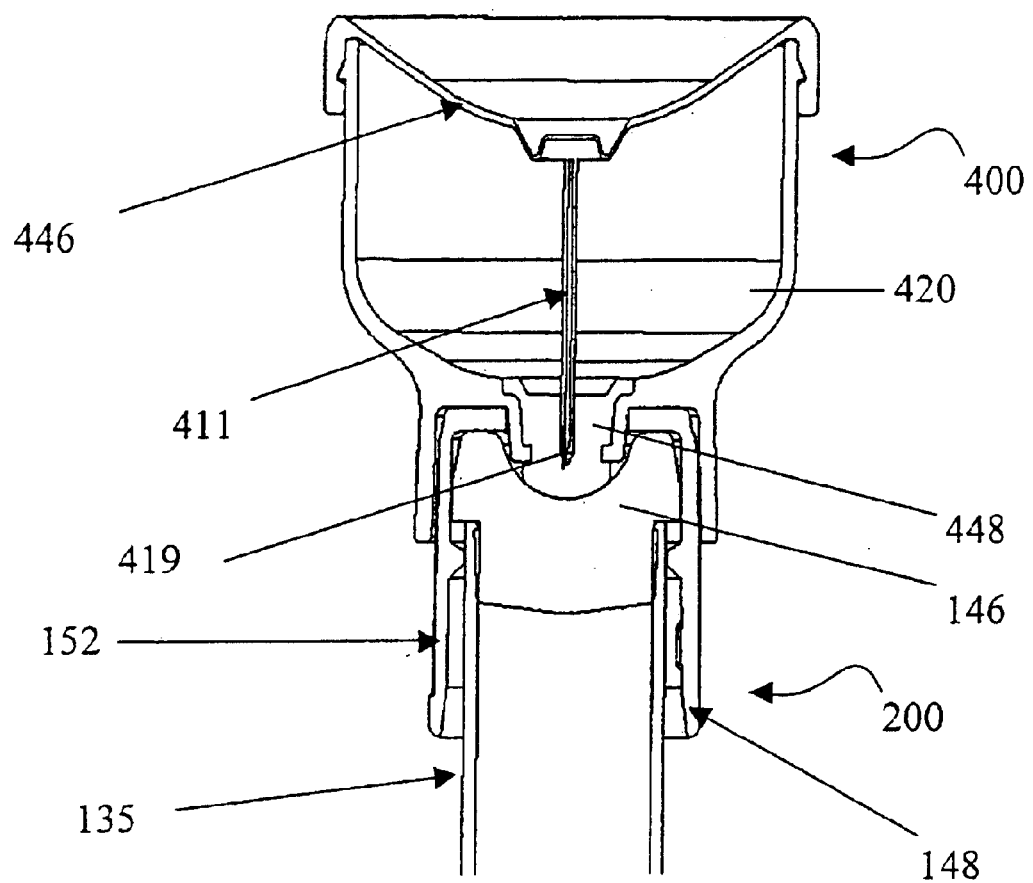
FIG. 8C is a schematic, cross-sectional view of a collection cell interfacing with a test tube assembly, according to another embodiment of the present invention, in which the collection cell is equipped with an extendable rubber stopper.

Collection cell 320 is further designed such that the level of fluid within collection cell 320 is below the level of the head of hollow needle 211. This prevents the contents of collection cell 320 from returning to primary tube 135 once the centrifugation process has been concluded FIG. 8C is a schematic, cross-sectional view of a collection cell assembly 400 interfacing with a test tube assembly 200, according to another embodiment of the present invention, in which collection cell 420 is sealed on top by an extendable rubber stopper or diaphragm 446. Hollow needle 411 forms an integral part of collection cell assembly 400, and is preferably held in place by seal 448 disposed at the bottom of collection cell 420 and fitting concentrically around needle 411.

As in FIG. 8A, primary tube 135 is sealed by rubber stopper 146. Flexible plastic lock 148 is preferably used to fix stopper 146 with respect to primary tube 135.

Hollow needle 411 is fixed by seal 448 such that the sharp end of needle 411 protrudes below collection cell 420, in the direction of rubber stopper 146. Protective skirt 152 envelops collection cell 420, with the bottom of skirt 152 extending below the sharp end of needle 411.

Initially, hollow needle 411 is disposed above the fluid-containing volume of primary tube 135 (either directly above rubber stopper 146, as shown, or within rubber stopper 146). Upon demand, diaphragm 446 is depressed, preferably by a plunger or another mechanism, such that needle 411 passes through rubber stopper 146, with the hollow, sharp end of needle 411 positioned within the fluid-containing volume of primary tube 135. Consequently, hollow needle 411 acts as a conduit for delivering a separated fraction from the sample in primary tube 135 to collection cell 420.

Figure 8D:
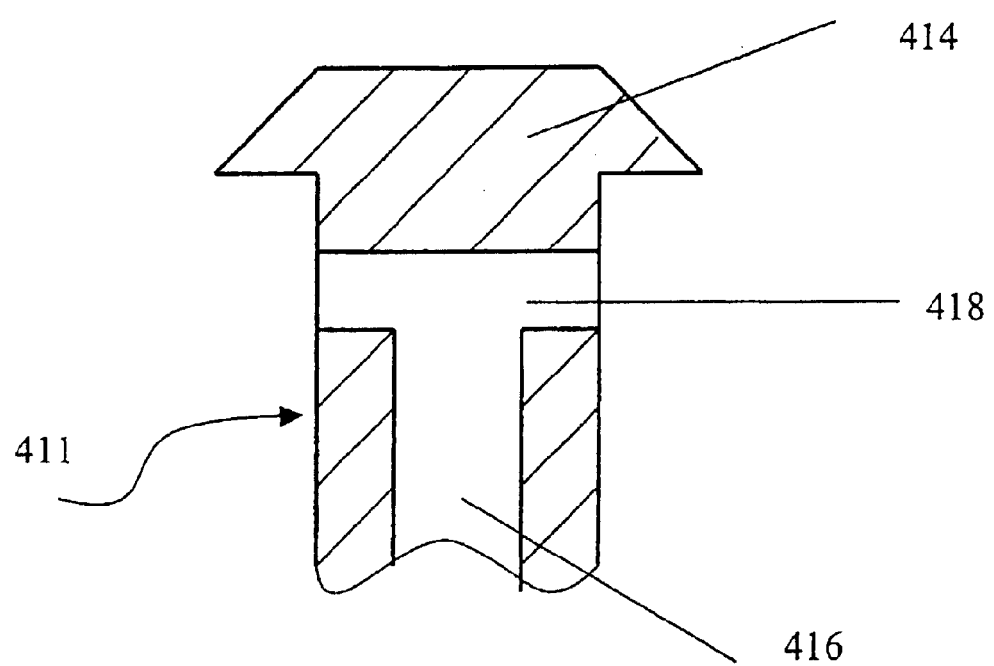
FIG. 8D is a schematic, cross-sectional view of a needle for use in conjunction with the collection cell of FIG. 8C.

FIG. 8D is a schematic, cross-sectional view of hollow needle 411. Preferably, needlehead 414 is sealed. Within needle 411 is a hollow channel 416, disposed substantially in parallel to needle 411. Preferably, hollow channel 416 has a T-shaped cross-section, with at least one opening 418 for fluid communication with collection cell 420. Thus, the separated fraction from the sample in primary tube 135 (see FIG. 8C) is discharged to collection cell 420 via opening 418, as has been described in greater detail hereinabove.

Upon completion of the transfer, diaphragm 446 is further depressed, so as to seal opening 418 in needle 411 by means of rubber stopper 146, such that the contents of collection cell 420 are not returned to primary tube 135. Alternatively, needle 411 can be raised such that an opening 419 near the sharp end of needle 411 is similarly sealed by rubber stopper 146.

Sampling of the separated fraction in collection cell 420 is preferably performed by penetration of upper stopper 446.

It must be emphasized that in all of the embodiments described herein, the interface between the collection cell and the test tube assembly can be designed in such a way that once a specimen is segregated, the cells and tubes remain connected, so as to prevent exposure of the sharp end of the needle as well as to prevent the dripping of fluid.

It must be emphasized that in the embodiments provided in FIGS. 8A–8C, the collecting cells may be part of a collection ring (either an integral part, or inserted therein). Alternatively, individual collection cells may be used. This is especially useful when the centrifuge is not completely filled each time it is spun. The collection cells provided in FIGS. 8A–8C can be individually loaded into the centrifuge by a cartridge. A robotic arm places each collection cell above a respective sample tube that has been inserted into lower ring 123. It will be appreciated by one skilled in the art that different embodiments may require different extensions or interfaces of ring 123 in order to properly locate the cells.

Figure 9A:
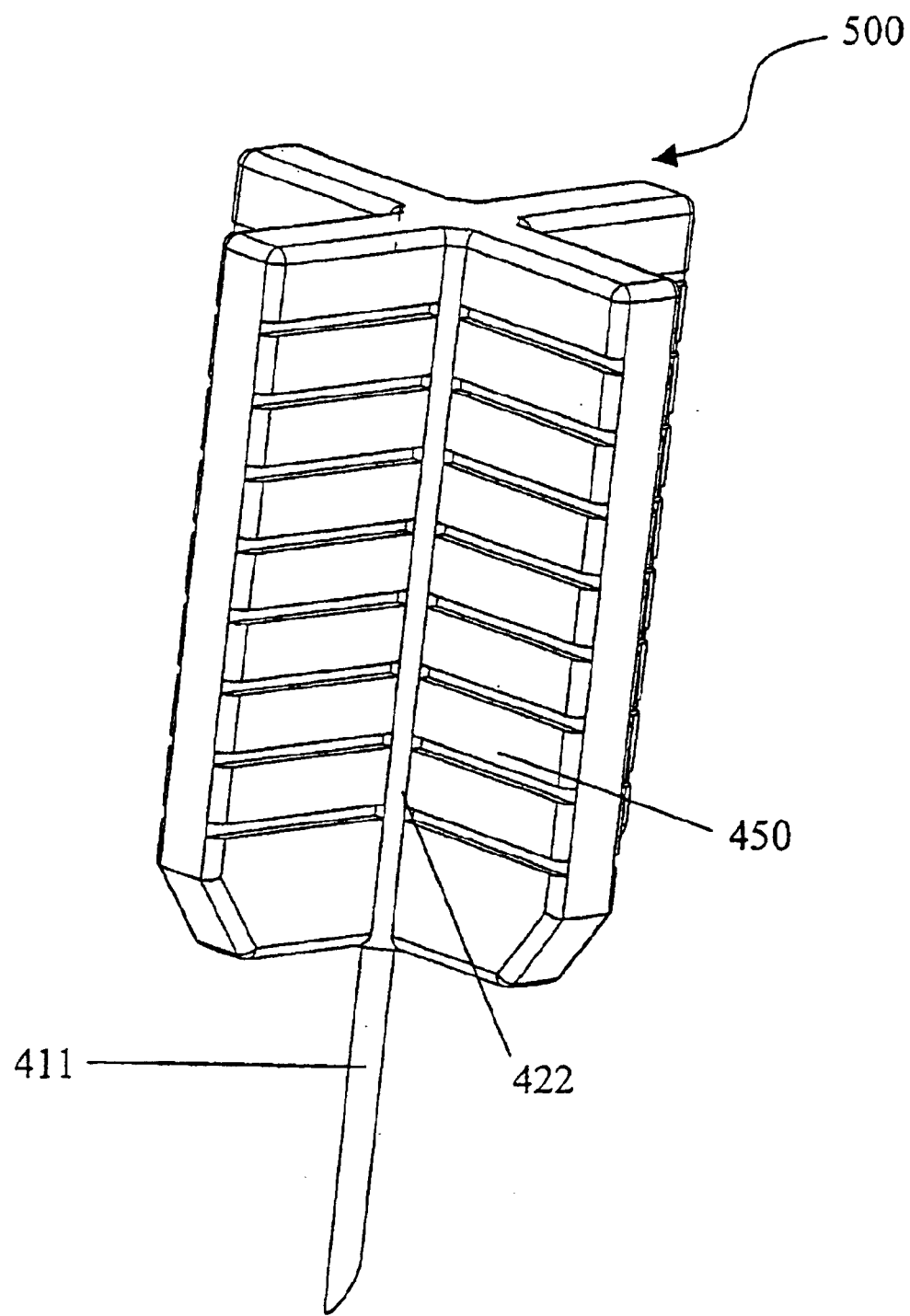
FIG. 9A is a schematic perspective view of a collection cell having a micro-analyzing functionality for in-situ analysis, according to yet another embodiment of the present invention.
Figure 9B:
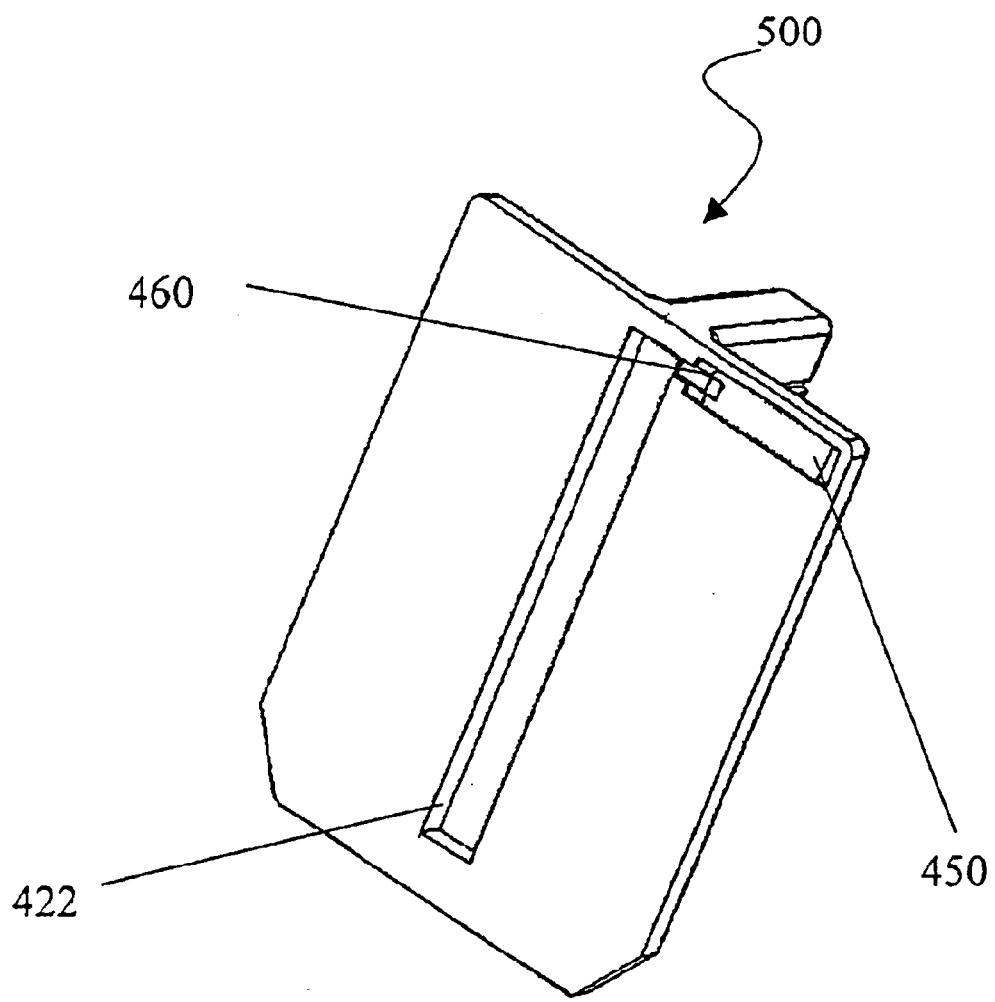
FIG. 9B is a schematic, cut-away view of a portion of the collection cell of FIG. 9A.

According to another embodiment of the present invention, the separation device is equipped with an analytical extension, preferably disposed within the volume of the collection cell, for in-situ analysis of the separated sample. A schematic perspective view of such a collection cell 500 is provided in FIG. 9A. A schematic cut-away view of a portion of collection cell 500 is illustrated in FIG. 9B. The serum/plasma flowing up through needle 411 is introduced into a central volume 422, and is subsequently diverted into a plurality of micro-cells 450 through micro-channels 460 (shown in FIG. 9B) extending from central volume 422. At the end of each micro-channel 460 (where micro-channel 460 connects to micro-cell 450), there is a flap 460A that prevents the backflow of liquid to central volume 422 at the end of the centrifugation. Each micro-cell 450 contains at least one reagent, as needed, for the determination of a specific analyte.

Figure 9C:
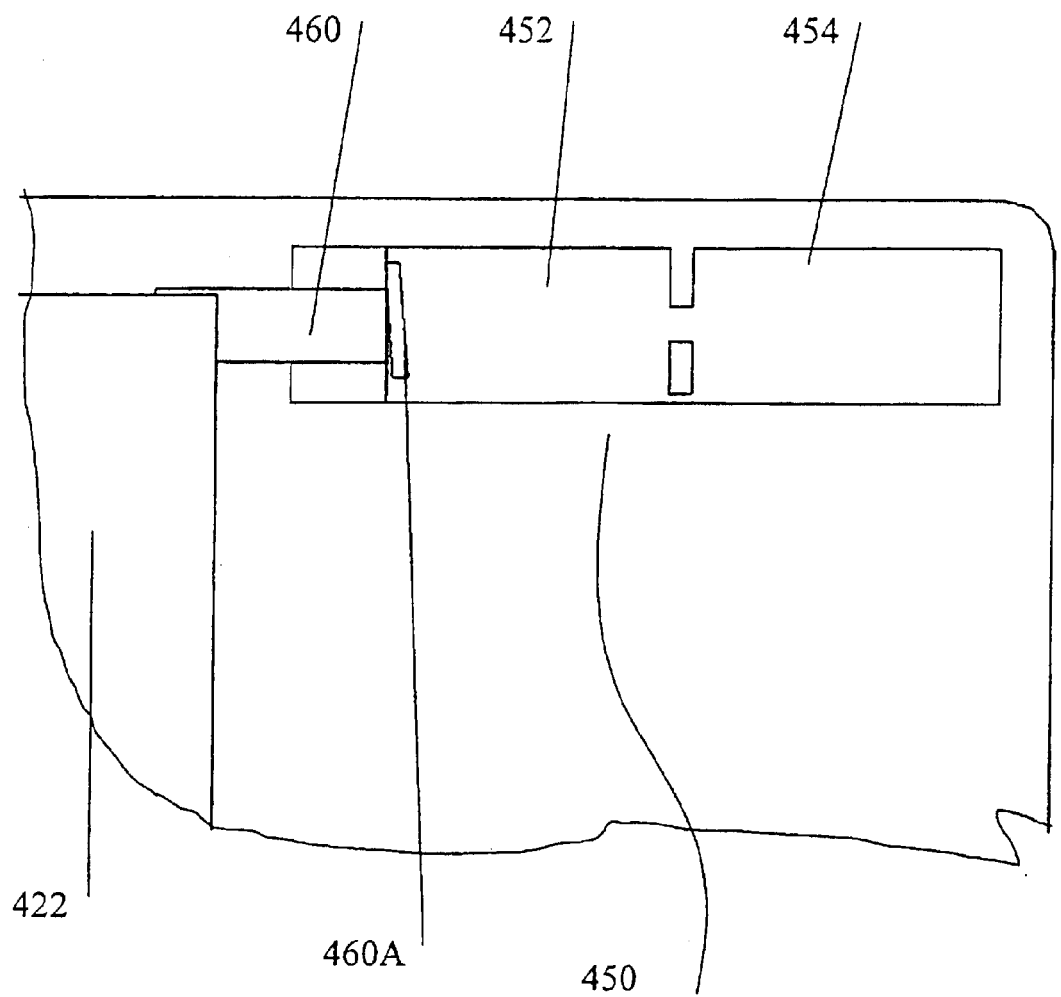
FIG. 9C is a magnified, schematic, cross-sectional view of a portion of the collection cell of FIG. 9B.

FIG. 9C is a magnified, schematic, cross-sectional view of a portion of the collection cell of FIG. 9B. At the entrance to micro-cell 450, the mouth of micro-channel 460 is equipped with flap 460A, which is designed to close off micro-cell 450 from micro-channel 460 when the pressure in micro-cell 450 is equal to the pressure of the fluid in micro-channel 460.

It should be emphasized that flap 460A is an exemplary embodiment of a valve designed to inhibit a reverse flow of the sample within collection cell 500, and that a wide variety of alternative designs and configurations will be apparent to one skilled in the art. It is to be further emphasized that the location of the valve could be anywhere within collection cell 500 or even within the needle connected thereto, because a state of fluid communication exists throughout the volume.

Micro-cell 450 preferably includes a first volume 452 containing at least one reagent, and a second volume 454 for containing compressed air, as a result of the displacement of air from first volume 452, and from micro-channel 460, etc., due to the elevated pressure from the centrifugation. Volume 454 may also contain any overflow of serum or plasma from first volume 452.

Each micro-channel 460 and micro-cell 450 is preferably designed according to the requisite volumes for the reagent (s), fluid (serum/plasma) and compressed air (i.e., air compressed by the sample fluid). Since the total volume of the micro-channels and micro-cells is much smaller that the volume of the plasma/serum fraction of the sample, most of the fluid remains in the primary tube, thus the pressure exerted by the fluid remains high, and provides significant compression of the air in each micro-channel 460 and micro-cell 450.

It may be advantageous to have an additional, complementary reagent in the micro-channels, such that the plasma/serum flowing from central volume 422 mixes with the reagent in micro-channel 460 before reacting with at least one reagent disposed in micro-cell 450 communicating therewith.

Collection cell 500 is preferably designed and configured to interface with test tube assembly 200 (shown in FIG. 8A) in a similar manner to other embodiments of the collection cell described hereinabove. It will be apparent to one skilled in the art that various designs and configurations of collection cell 500 can be implemented to effect the microanalysis, and to securely interface collection cell 500 with test tube assembly 200.

Preferably, each microanalysis performed within collection cell 500 is based on a calorimetric reaction of the reagent in each micro-cell 450.

Thus, in the above-described system and method, the analytical process may be carried out within collection cell 500 directly upon separation and segregation of plasma/serum, eliminating thereby the need to transfer the sample to an external analytical device. In addition to saving a substantial amount of time, this device and method assure the positive identification of the sample with a particular patient and provide maximum safety for the operator.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, no citation or identification of any reference in this application shall be construed as an admission that such reference is available as prior art to the present invention.

What is claimed is:

1. A system for separating fluids by centrifuging, the system comprising:
   a rotor assembly for rotating in a centrifugation device, said rotor assembly including:
   (a) a first rotor for housing at least one container, each said container containing a sample for separation by centrifuging;
   (b) a second rotor having at least one collection compartment, each compartment corresponding to a particular container of said at least one container, and
   (c) at least one conduit, each conduit corresponding to a particular compartment of said at least one compartment, each conduit for providing fluid communication, upon demand, between said particular container and said particular compartment, so as to enable transfer of a separated fraction of each said sample from said container into said compartment,
   wherein said collection compartment is designed for fluid communication with an ambient environment, so as to operate at a substantially ambient pressure during the centrifuging and during a filling of said collection compartment with said separated fraction.

2. The system of claim 1, wherein said transfer is a complete transfer of said separated fraction to the collection compartment.

3. The system of claim 1, wherein said compartment has a first opening for said fluid communication between said conduit and said compartment, and wherein said compartment has a second opening for withdrawing at least a portion of said fraction therefrom.

4. The system of claim 3, wherein said second opening is disposed outside of said conduit.

5. The system of claim 3, wherein said second opening is disposed, with respect to said conduit, on a different face of said compartment.

6. The system of claim 3, wherein said second opening is recessed in a face of said compartment, so as to receive a probe.

7. The system of claim 1, wherein said particular conduit and said compartment corresponding thereto, form a monolithic element.

8. The system of claim 1, wherein said conduit includes a hollow needle having a single sharp end.

9. A system for separating fluids by centrifuging, the system comprising:
   (a) at least one collection compartment for rotating in a centrifugation device, each said compartment for receiving a fraction of a sample separated by said centrifugation device, each said compartment including:
   (i) at least one micro-cell, each said micro-cell containing a reagent for effecting an analytical determination on said fraction of said sample, and
   (b) at least one conduit, each said conduit corresponding to a particular compartment of said at least one collection compartment, each said conduit for transferring said fraction, during a rotation of said centrifugation device, to said compartment.

10. The system of claim 9, wherein each said compartment further includes:
   (ii) at least one micro-channel, each said micro-channel for delivering at least a portion of said fraction to a particular one of said at least one micro-cell.

11. The system of claim 10, wherein said micro-channel is designed to receive a second reagent, such that a flow of said sample mixes with said second reagent in said micro-channel prior to reacting with said reagent in said micro-cell.

12. The system of claim 10, wherein said micro-channel has a valve for preventing a return flow from said micro-cell.

13. The system of claim 12, wherein said valve is a flap.

14. The system of claim 12, wherein said valve is responsive to a pre-determined pressure differential so as to automatically close said micro-channel.

15. The system of claim 10, wherein said micro-channel has a valve for preventing a return flow of said sample to a central sample volume disposed within said compartment.

16. The system of claim 10, further including a valve, associated with said compartment, for preventing a return flow within said compartment.

17. The system of claim 10, further including a valve, disposed within said compartment, for preventing a return flow within said compartment.

18. The system of claim 9, wherein each said compartment further includes:
   a rotor assembly for rotating in a centrifugation device, said rotor assembly for housing said at least one collection compartment.

19. The system of claim 9, wherein said conduit is integral to said collection compartment.

20. The system of claim 9, wherein said conduit is a hollow needle.

21. The system of claim 9, wherein said at least one micro-cell is a plurality of micro-cells.

22. The system of claim 9, wherein said at least one collection compartment has an interface for interfacing with a sample holder assembly.

23. The system of claim 9, the system further comprising:
   (c) a sample holder assembly having a sample holder, said assembly for rotating in said centrifugation device so as to produce said fraction of said sample, said sample holder fluidly communicating with said conduit, upon demand.

24. The system of claim 9, wherein said sample is a blood sample.

25. The system of claim 9, wherein said at least one micro-cell includes a first volume for containing said reagent, and a second volume, fluidly communicating with said first volume, for containing air compressed during said rotation of said centrifugation device.

26. A system for separating fluids by centrifuging, the system comprising:
   a rotor assembly far rotating in a centrifugation device, said rotor assembly including:
   (a) a first rotor for housing at least one container, each said container containing a sample for separation by centrifuging;
   (b) a second rotor having at least one collection compartment, each compartment corresponding to a particular container of said at least one container, and
   (c) at least one conduit, each conduit corresponding to a particular compartment of said at least one compartment, each conduit for providing fluid communication, upon demand, between said particular container and said particular compartment, so as to enable transfer of a separated fraction of each said sample from said container to said compartment, wherein said conduit is affixed to said second rotor.

27. The system of claim 26, wherein said at least one compartment is a plurality of compartments, and wherein said at least one conduit is a plurality of conduits.

28. A system for separating fluids by centrifuging, the system comprising:

a rotor assembly for rotating in a centrifugation device, said rotor assembly including:

(a) a first rotor for housing at least one container, each said container containing a sample for separation by centrifuging;

(b) a second rotor having at least one collection compartment, each compartment corresponding to a particular container of said at least one container, and (c) at least one conduit, each conduit corresponding to a particular compartment of said at least one compartment, each conduit for providing fluid communication, upon demand, between said particular container and said particular compartment, so as to enable transfer of a separated fraction of each said sample from said container to said compartment, wherein said collection compartment is defined by a contour of a wall of said second rotor.

29. The system of claim 28, wherein said compartment has a first opening for said fluid communication between said conduit and said compartment, and wherein said compartment has a second opening for withdrawing at least a portion of said fraction therefrom.

30. The system of claim 29, wherein said second opening is disposed, with respect to said conduit, on a different face of said compartment.

31. A system for separating fluids by centrifuging, the system comprising:

a rotor assembly for rotating in a centrifugation device, said rotor assembly including:

(a) a first rotor for housing at least one container, each said container containing a sample for separation by centrifuging;

(b) a second rotor having at least one collection compartment, each compartment corresponding to a particular container of said at least one container, and (c) at least one conduit, each conduit corresponding to a particular compartment of said at least one compartment, each conduit for providing fluid communication, upon demand, between said particular container and said particular compartment, so as to enable transfer of a separated fraction of each said sample from said container to said compartment, wherein said collection compartment has a first opening for said fluid communication between said conduit and said compartment, and wherein said compartment has a second opening for withdrawing at least a portion of said fraction therefrom.

32. The system of claim 31, wherein said second opening is disposed outside of said conduit.

33. The system of claim 31, wherein said second opening is disposed, with respect to said conduit, on a different face of said compartment.

34. The system of claim 31, wherein said second opening is recessed in a face of said compartment, so as to receive a probe.

35. The system of claim 31, wherein said conduit includes a hollow needle, and wherein said second rotor further includes at least one shielding element, each element designed, in a first configuration, to shield a point of said needle.

36. The system of claim 35, wherein said at least one shielding element is designed, in a second configuration, to reveal said point of said needle.

37. The system of claim 35, wherein said at least one shielding element is spring-loaded.

38. The system of claim 31, wherein said first rotor has at least one slot in a side face, to allow reading of an identification label on said container.

39. The system of claim 31, wherein said second rotor is designed to be reversibly detached from said centrifugation device.

40. The system of claim 31, wherein said first rotor and said second rotor are detachably attached, so as to be removed from said centrifugation device as a single unit.

41. The system of claim 31, wherein each compartment includes at least one micro-cell containing a reagent for effecting an analytical determination on said fraction of said sample.

42. The system of claim 31, wherein said at least one compartment is a plurality of compartments, and wherein said at least one conduit is a plurality of conduits.

43. A method for separating fluids by centrifuging, comprising the steps of:

(a) providing a rotor assembly for a centrifugation device, said rotor assembly including:

(i) a first rotor for housing at least one container, each said container containing a sample for separation by centrifuging;

(ii) a second rotor having at least one collection compartment, each compartment corresponding to a particular container of said at least one container, and (iii) at least one conduit, each conduit corresponding to a particular compartment of said at least one compartment, each conduit for providing fluid communication, upon demand, between said particular container and said particular compartment, wherein said collection compartment has a first opening for said fluid communication between said conduit and said compartment, and wherein said compartment has a second opening for withdrawing at least a portion of said fraction therefrom;

(b) rotating said rotor assembly, and (c) transferring a separated fraction of each said sample from said container to said compartment.

44. The method of claim 43, further comprising the step of:

(d) sampling from said collection compartment while said compartment is disposed in said second rotor.

45. The method of claim 43, further comprising the steps of:

(d) loading said at least one container into said first rotor, and (e) affixing, subsequent to step (d), said second rotor in said rotor assembly of said centrifugation device.

46. The method of claim 45, wherein said loading is performed prior to affixing said first rotor within said centrifugation device.

47. The method of claim 43, further comprising the step of:

(d) after said rotating of said rotor assembly, removing said first rotor, said conduit, and said second rotor as a single unit.

48. The method of claim 43, further comprising the step of:

(d) after said rotating of said rotor assembly, removing said compartment, said conduit, and said container as a single unit.

* * * * *